United States Patent
Yamada et al.

(10) Patent No.: US 9,775,354 B2
(45) Date of Patent: Oct. 3, 2017

(54) HERBICIDAL COMPOSITION HAVING IMPROVED PLANT SAFETY

(71) Applicant: ISHIHARA SANGYO KAISHA, LTD., Osaka (JP)

(72) Inventors: Ryu Yamada, Shiga (JP); Yoshikazu Satake, Shiga (JP)

(73) Assignee: ISHIHARA SANGYO KAISHA, LTD., Osaka (JP)

( * ) Notice: Subject to any disclaimer, the term of this patent is extended or adjusted under 35 U.S.C. 154(b) by 0 days.

(21) Appl. No.: 14/894,717

(22) PCT Filed: Jun. 26, 2014

(86) PCT No.: PCT/JP2014/067013
§ 371 (c)(1),
(2) Date: Nov. 30, 2015

(87) PCT Pub. No.: WO2014/208674
PCT Pub. Date: Dec. 31, 2014

(65) Prior Publication Data
US 2016/0100580 A1 Apr. 14, 2016

(30) Foreign Application Priority Data
Jun. 27, 2013 (JP) ................................. 2013-134466

(51) Int. Cl.
A01N 47/06 (2006.01)
A01N 41/06 (2006.01)
A01N 43/42 (2006.01)
A01N 43/56 (2006.01)
A01N 43/653 (2006.01)
A01N 43/80 (2006.01)

(52) U.S. Cl.
CPC ............. *A01N 47/06* (2013.01); *A01N 41/06* (2013.01); *A01N 43/42* (2013.01); *A01N 43/56* (2013.01); *A01N 43/653* (2013.01); *A01N 43/80* (2013.01)

(58) Field of Classification Search
None
See application file for complete search history.

(56) References Cited

U.S. PATENT DOCUMENTS

| | | |
|---|---|---|
| 8,003,569 B2 | 8/2011 | Witschel et al. |
| 8,435,928 B2 | 5/2013 | Kikugawa et al. |
| 8,466,089 B2 | 6/2013 | Tsukamoto et al. |
| 8,492,310 B2 | 7/2013 | Kikugawa et al. |
| 2003/0032559 A1 | 2/2003 | Ziemer et al. |
| 2003/0158039 A1 | 8/2003 | Schmitt et al. |
| 2004/0087445 A1 | 5/2004 | Ziemer et al. |
| 2004/0248736 A1 | 12/2004 | Schmitt et al. |
| 2006/0234862 A1 | 10/2006 | Huff et al. |
| 2007/0060478 A1 | 3/2007 | Witschel et al. |
| 2009/0023588 A1 | 1/2009 | Witschel et al. |
| 2011/0319266 A1 | 12/2011 | Yamato et al. |
| 2015/0216165 A1 | 8/2015 | Kikugawa et al. |

FOREIGN PATENT DOCUMENTS

| | | | |
|---|---|---|---|
| JP | 2009-040771 A | 2/2009 | |
| JP | WO 2009142318 A1 * | 11/2009 | ........... C07D 231/20 |
| JP | 2010-159247 A | 7/2010 | |
| JP | 2010-180198 A | 8/2010 | |
| JP | 2014-028796 A | 2/2014 | |
| WO | 2004/080172 A1 | 9/2004 | |

OTHER PUBLICATIONS

Taylor et al., Protective responses induced by herbicide safeners in wheat, Environmental and Experimental Botany (2013), Vo. 88, pp. 93-99 (available online Jan. 16, 2012).*
"Shibuya Index 16th Edition", May 1, 2012, pp. 253-254.
International Search Report issued with respect to application No. PCT/JP2014/067013, dated Sep. 16, 2014.
International Preliminary Report on Patentability issued with respect to application No. PCT/JP2014/067013, dated Jan. 7, 2016.
European Search Report issued with respect to application No. 14818007.8, dated Oct. 17, 2016.

* cited by examiner

*Primary Examiner* — Hasan Ahmed
*Assistant Examiner* — Frank Choi
(74) *Attorney, Agent, or Firm* — Greenblum & Bernstein, P.L.C.

(57) ABSTRACT

To provide a herbicidal composition which has a high herbicidal effect against undesired plants while stably maintaining the safety for useful plants, independently of various conditions such as weather conditions, soil conditions, varieties of the crop plants, and the timing for the application of the herbicide.

A herbicidal composition comprising (1) 1-(1-ethyl-4-(3-(2-methoxyethoxy)-2-methyl-4-(methylsulfonyl)benzoyl)-1H-pyrazol-5-yloxy)ethyl methyl carbonate or its salt and (2) at least one compound selected from the group consisting of fenchlorazole-ethyl, isoxadifen-ethyl, mefenpyr-diethyl, cloquintocet-mexyl and cyprosulfamide.

12 Claims, No Drawings

HERBICIDAL COMPOSITION HAVING IMPROVED PLANT SAFETY

TECHNICAL FIELD

The present invention relates to a herbicidal composition having improved safety for useful plants.

BACKGROUND ART

So-called selective herbicides having both safety for useful plants and herbicidal effects against undesired plants are actively used, but in actual use, even a highly selective herbicide has undesired effects against useful plants (simply referred to as phytotoxicity in many cases) depending upon various conditions such as weather conditions, soil conditions, varieties of the crop plants and the timing for the application of the herbicide in some cases. To cope with such an undissipated situation, use of various safeners has been studied, but the selection of the safener varies depending upon the type of the herbicide with which the safener is used in combination and depends on trial and error studies. For example, Patent Document 1 discloses herbicidal mixtures comprising cloquintocet as a safener.

PRIOR ART DOCUMENT

Patent Document

Patent Document 1: WO2004/080172

DISCLOSURE OF INVENTION

Technical Problem

A herbicidal composition which has a high herbicidal effect against undesired plants while stably maintaining the safety for useful plants independent of various conditions such as weather conditions, soil conditions, varieties of the crop plants and the timing for the application of the herbicide, has been desired.

Solution to Problem

The present inventors have conducted extensive studies to achieve the above object and as a result, found a herbicidal composition having both safety for useful plants and herbicidal effect against undesired plants, by use of a herbicidal pyrazole type compound and a specific compound in combination, and accomplished the present invention.

That is, the present invention relates to a herbicidal composition comprising (1) 1-(1-ethyl-4-(3-(2-methoxyethoxy)-2-methyl-4-(methylsulfonyl)benzoyl)-1H-pyrazol-5-yloxy)ethyl methyl carbonate (hereinafter referred to as compound A) or its salt and (2) at least one compound selected from the group consisting of fenchlorazole-ethyl, isoxadifen-ethyl, mefenpyr-diethyl, cloquintocet-mexyl and cyprosulfamide (hereinafter referred to as compound B). The present invention further relates to a method for controlling undesired plants, which comprises applying a herbicidally effective amount of compound A and an amount effective as a safener of compound B, to the undesired plants or to a place where they grow. The present invention further relates to a method for improving the safety of compound A for useful plants by compound B, in other words, a method for reducing an undesired effect of compound A against useful plants by compound B.

Advantageous Effects of Invention

According to the present invention, a herbicidal composition which has a high herbicidal effect against undesired plants while stably maintaining the safety for useful plants, independent of various conditions such as weather conditions, soil conditions, varieties of the crop plants, and the timing for the application of the herbicide, can be provided.

DESCRIPTION OF EMBODIMENTS

The present invention is carried out, for example, in such a manner that compound A or its salt which is a herbicidal pyrazole type compound is formulate with various additives and diluted with e.g. water together with compound B, and the resulting formulation is applied to undesired plants or to a place where they grow. Further, the present invention is carried out, for example, in such a manner that compound A or its salt and compound B are formulated together with various additives, and the resulting formulation as diluted with e.g. water or without being diluted is applied to undesired plants or to a place where they grow.

In the present invention, compound A or its salt may be applied and then compound B is applied, or compound B may be applied and then compound A or its salt is applied.

In the present invention, the herbicidal composition may be applied at any time before or after the emergence of undesired plants.

Compound A is a known compound disclosed in WO2009/142318 (compound No. 2-1).

The salt of compound A includes all the agriculturally acceptable salts, and it may, for example, be an alkali metal salt such as a sodium salt or a potassium salt; an alkaline earth metal salt such as a magnesium salt or a calcium salt; an amine salt such as a dimethylamine salt or a triethylamine salt; an inorganic acid salt such as a hydrochloride, a perchlorate, a sulfate or a nitrate; or an organic acid salt such as an acetate or a methanesulfonate.

Fenchlorazole-ethyl, isoxadifen-ethyl, mefenpyr-diethyl, cloquintocet-mexyl and cyprosulfamide as compound B are known compounds having the following chemical structures.

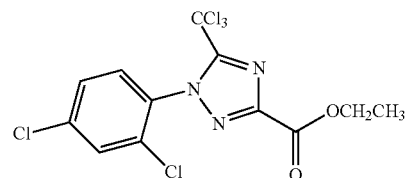

Fenchlorazole-ethyl

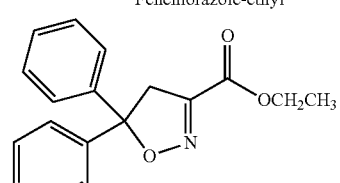

Isoxadifen-ethyl

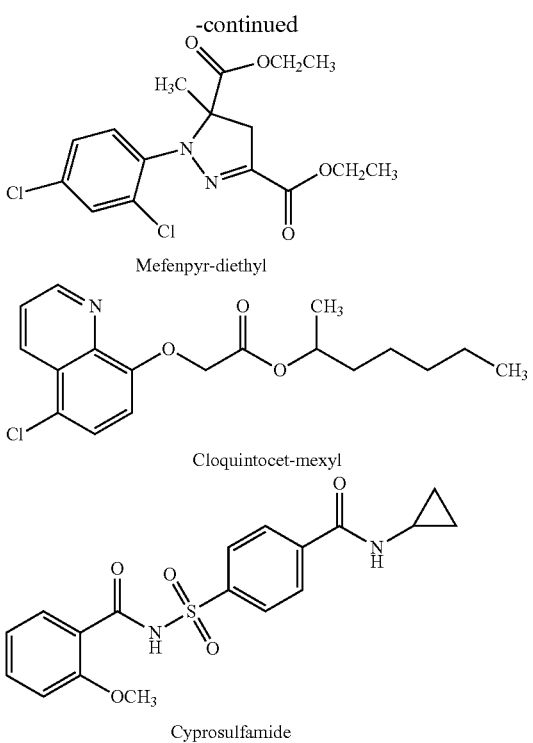

Mefenpyr-diethyl

Cloquintocet-mexyl

Cyprosulfamide

When the above compounds as compound B have a structural isomer, a salt, a hydrate or the like, they are all included in the present invention.

The mixing ratio of compound A or its salt to compound B in the present invention cannot generally be defined, since it varies depending upon the weather conditions, the type and the growth stage of plants to be controlled, the type and the growth stage of useful plants, the formulation, the type of compound B, etc., and for example, it is preferably from 1:0.05 to 1:2, more preferably from 1:0.1 to 1:1, further preferably from 1:0.1 to 1:0.5, as represented by the weight ratio of compound A or its salt:compound B.

The application amount of compound A or its salt in the present invention cannot generally be defined, since it varies depending upon the weather conditions, the type and the growth stage of plants to be controlled, the type and the growth stage of useful plants, the formulation, the type of compound B, etc., and for example, it is preferably from 5 to 150 g/ha, more preferably from 10 to 150 g/ha, further preferably from 50 to 150 g/ha. The application amount of compound B may properly be selected to achieve the above-mentioned mixing ratio of compound A or its salt to compound B. The application amount of compound B cannot generally be defined in the same manner as the case of compound A or its salt, and for example, it is preferably from 0.25 to 300 g/ha, more preferably from 1 to 100 g/ha, further preferably from 10 to 75 g/ha. Further, when the above application amounts of compound A or its salt and compound B are applied as diluted with water for example, the amount of water is preferably from 20 to 3,000 L/ha, more preferably from 30 to 2,000 L/ha.

The herbicidal composition of the present invention is effectively used to selectively control noxious weeds which are undesired plants in cultivation or growth control of useful plants, for example, corn (*Zea mays* L.), soybean (*Glycine max* Merr.), cotton (*Gossypium* spp.), wheat (*Triticum* spp.), rice (*Oryza sativa* L.), barley (*Hordeum Vulgare* L.), rye (*Secale cereale* L.), oat (*Avena sativa* L.), sorgo (*Sorghum bicolor* Moench), rape (*Brassica napus* L.), sunflower (*Helianthus annuus* L.), suger beet (*Beta Vulgaris* L.), suger cane (*Saccharum officinarum* L.), japanese lawngrass (*Zoysia japonica* stend), kentucky bluegrass (*Poa pratensis* L.), perennial ryegrass (*Lolium perenne* L.), bentgrass (*Agrostis stolonifera* L.), timothy (*Phleum pratense* L.), orchardgrass (*Dactylis glolmerata* L.), peanut (*Arachis hypogaea* L.), flax (*Linum usitatissimum* L.), tobacco (*Nicotiana tabacum* L.), coffee (*Coffea* spp.), etc., while maintaining the safety for such useful plants. Particularly, the herbicidal composition of the present invention is effectively used to selectively control noxious weeds in cultivation or growth control of corn, wheat, suger cane, kentucky bluegrass, perennial ryegrass, bentgrass, timothy, orchardgrass, sorgo, etc. Particularly, the herbicidal composition of the present invention is effectively used to selectively control noxious weeds in cultivation or growth control of corn, wheat, kentucky bluegrass, perennial ryegrass, bentgrass, timothy, etc. Particularly, the herbicidal composition of the present invention is effectively used to selectively control noxious weeds in cultivation or growth control of wheat, kentucky bluegrass, perennial ryegrass, bentgrass, timothy, etc.

"Maintaining the safety for useful plants" means not to cause an undesired effect against the useful plants, for example, discoloring, brown discoloration, necrosis, chlorosis, anthocyan or growth inhibition, or to reduce such an undesired effect to a practically negligible level.

In growth control of lawn such as kentucky bluegrass, perennial ryegrass or bentgrass, an undesired effect which develops in such lawn, particularly discoloring, brown discoloration, necrosis, chlorosis, anthocyan or the like, causes a serious problem even though it is very slight. Specifically, even if the affected area is slight in one leaf, the overall landscape will be significantly impaired in a case where the lawn is planted in a wide range and its growth is controlled, e.g. in golf courses or football grounds assumed as actual use. Further, if the growth of the lawn is inhibited, the height or the like of the lawn tends to be non-uniform, and the overall landscape of e.g. golf courses or football grounds will significantly be impaired in the same manner as above. The herbicidal composition of the present invention is effectively used to control noxious weeds without causing the undesired effect or while significantly reducing the undesired effect in various sites where the lawn is used.

Further, in cultivation of crop plants such as corn or wheat or grass such as timothy, if the growth is inhibited, the yield of the crop plants of the like will be impaired. The herbicidal composition of the present invention is effectively used to control noxious weeds without causing the undesired effect or while significantly reducing the undesired effect in cultivation of useful crop plants such as corn or wheat or grass such as timothy.

The undesired plants, i.e. noxious weeds, which can be controlled by the herbicidal composition of the present invention may, for example, be gramineae such as barnyardgrass (*Echinochloa crus-galli* L., *Echinochloa oryzicola* vasing.), crabgrass (*Digitaria sanguinalis* L., *Digitaria ischaemum* Muhl., *Digitaria adscendens* Henr., *Digitaria microbachne* Henr., *Digitaria horizontalis* Willd.), green foxtail (*Setaria viridis* L.), giant foxtail (*Setaria faberi* Herrm.), yellow foxtail (*Setaria lutescens* Hubb.) gooseg-rass (*Eleusine indica* L.), wild oat (*Avena fatua* L.), johnsongrass (*Sorghum halepense* L.), quackgrass (*Agropyron repens* L.), alexandergrass (*Brachiaria plantaginea* (Link) Hitchc.), guineagrass (*Panicum maximum* Jacq.), paragrass (*Panicum purpurascens* Raddi), sprangletop (*Leptochloa chinensis* (L.) Nees), red sprangletop (*Leptochloa panicea* (Retz.) Ohwi), annual bluegrass (*Poa annus* L.), black grass (*Alopecurus myosuroides* Huds.), cholorado bluestem (*Agropyron tsukushiense* (Honda) Ohwi), broadleaf signalgrass (*Brachiaria platyphylla* Nash), southern sandbur (*Cenchrus echinatus* L.), italian ryegrass (*Lolium multiflorum* Lam.), or bermudagrass (*Cynodon dactylon* Pers.); cyperaceae such as rice flatsedge (*Cyperus iria* L.), purple nutsedge (*Cyperus rotundus* L.), or yellow nutsedge (*Cyperus esculentus* L.); alismataceae such as Japanese ribbon waparo (*Sagittaria pygmaea* Miq.) or arrow-head (*Sagittaria trifolia* L.); pontederiaceae such as monochoria (*Monochoria vaginalis* var. *plantaginea* (Burm. f.) Kunth); scrophulariaceae such as persian speedwell (*Veronica persica* Poir.) or corn speedwell (*Veronica arvensis* L.); malvaceae such as velvetleaf (*Abutilon theophrasti* MEDIC.) or prickly *sida* (*Sida spinosa* L.); compositae such as common cocklebur (*Xanthium strumarium* L.), common ragweed (*Ambrosia elatior* L.), horseweed (*Erigeron canadensis* L.), shiny cudweed (*Gnaphalium spicatum* Lam.), thistle (*Breea setosa* (BIEB.) KITAM.), hairy *galinsoga* (*Galinsoga ciliata* Blake), wild chamomile (*Matricaria chamomilla* L.); solanaceae such as black nightshade (*Solanum nigrum* L.) or jimsonweed (*Datura stramonium* L.); amaranthaceae such as prostrate pigweed (*Amaranthus blitoides* S. Wats.), livid amaranth (*Amaranthus lividus* L.), purple amaranth (*Amaranthus blitum* L.), smooth pigweed (*Amaranthus hybridus* L., *Amaranthus patulus* Bertol., powell amaranth (*Amaranthus powellii* S. Wats.), slender amaranth (*Amaranthus viridis* L.), palmer amaranth (*Amaranthus palmeri* S. Wats.), redroot pigweed (*Amaranthus retroflexus* L.), tall waterhemp (*Amaranthus tuberculatus* (Moq.) Sauer.), common waterhemp (*Amaranthus tamariscinus* Nutt.), thorny amaranth (*Amaranthus spinosus* L.), ataco (*Amaranthus quitensis* Kunth.) or *Amaranthus rudis* Sauer; polygonaceeae such as pale smartweed (*Polygonum lapathifolium* L.), ladysthumb (*Polygonum persicaria* L.), wild buckwheat (*Polygonum convolvulus* L.) or knotweed (*Polygonum aviculare* L.); cruciferae such as flexuous bittercress (*Cardamine flexuosa* WITH.), shepherd's-purse (*Capsella bursa-pastoris* Medik.) or indian mustard (*Brassica juncea* Czern.); convolvulaceae such as tall morningglory (*Ipomoea purpurea* L.), field bindweed (*Convolvulus arvensis* L.) or ivyleaf morning-glory (*Ipomoea hederacea* Jacq.); chenopodiaceae such as common lambsquarters (*Chenopodium album* L.) or mexican burningbush (*Kochia scoparia* Schrad.); portulacaceae such as common purslane (*Portulaca oleracea* L.); leguminosae such as common vetch (*Vicia angustifolia* L.) or sicklepod (*Cassia obtusifolia* L.); caryophyllaceae such as common chickweed (*Stellaria media* L.); labiatae such as henbit (*Lamium amplexicaule* L.) or purple deadnettle (*Lamium purpureum* L.); rubiaceae such as catchweed (*Galium spurium* L.); euphorbiaceae such as threeseeded copperleaf (*Acalypha australis* L.); commelinaceae such as common dayflower (*Commelina communis* L.); or geraniaceae such as carolina *geranium* (*Geranium carolinianum* L.).

The application range of the herbicidal composition of the present invention extends to crop plant fields, orchards and plantations. Further, the herbicidal composition of the present invention can effectively be used to selectively control noxious weeds in cultivation of various transgenic plants. Examples of the transgenic plants include insect resistant transgenic plants, plant disease-resistant transgenic plants, transgenic plants regarding the plant constituents, and herbicide-resistant transgenic plants.

In the present invention, a herbicidal compound other than compound A or its salt may be mixed if desired. Such another herbicidal compound may suitably be selected from the following compound groups (1) to (11) (common names or test codes). Even when not specifically mentioned here, in a case where such compounds have salts, alkyl esters, structural isomers such as optical isomers etc., they are, of course, all included.

(1) Those which are believed to exhibit herbicidal effects by disturbing hormone activities of plants, such as a phenoxy type such as 2,4-D, 2,4-D-butotyl, 2,4-D-butyl, 2,4-D-dimethylammonium, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl, mecoprop-P-potassium, naproanilide or clomeprop; an aromatic carboxylic acid type such as 2,3,6-TBA, dicamba, dicamba-butotyl, dicamba-diglycolamine, dicamba-dimethylammonium, dicamba-diolamine, dicamba-isopropylammonium, dicamba-potassium, dicamba-sodium, dichlobenil, picloram, picloram-dimethylammonium, picloram-isoctyl, picloram-potassium, picloram-triisopropanolammonium, picloram-triisopropylammonium, picloram-trolamine, triclopyr, triclopyr-butotyl, triclopyr-triethylammonium, clopyralid, clopyralid-olamine, clopyralid-potassium, clopyralid-triisopropanolammonium or aminopyralid; and others such as naptalam, naptalam-sodium, benazolin, benazolin-ethyl, quinclorac, quinmerac, diflufenzopyr, diflufenzopyr-sodium, fluroxypyr, fluroxypyr-2-butoxy-1-methylethyl, fluroxypyr-meptyl, chlorflurenol, chlorflurenol-methyl, aminocyclopyrachlor, aminocyclopyrachlor-methyl or aminocyclopyrachlor-potassium.

(2) Those which are believed to exhibit herbicidal effects by inhibiting photosynthesis of plants, such as a urea type such as chlorotoluron, diuron, fluometuron, linuron, isoproturon, metobenzuron, tebuthiuron, dimefuron, isouron, karbutilate, methabenzthiazuron, metoxuron, monolinuron, neburon, siduron, terbumeton, trietazine or metobromuron; a triazine type such as simazine, atrazine, atratone, simetryn, prometryn, dimethametryn, hexazinone, metribuzin, terbuthylazine, cyanazine, ametryn, cybutryne, triaziflam, indaziflam, terbutryn, propazine, metamitron or prometon; a uracil type such as bromacil, bromacyl-lithium, lenacil or terbacil; an anilide type such as propanil or cypromid; a carbamate type such as swep, desmedipham or phenmedipham; a hydroxybenzonitrile type such as bromoxynil, bromoxynil-octanoate, bromoxynil-heptanoate, ioxynil, ioxynil-octanoate, ioxynil-potassium or ioxynil-sodium; and others such as pyridate, bentazone, bentazone-sodium, amicarbazone, methazole or pentanochlor.

(3) Quaternary ammonium salt type such as paraquat or diquat, which is believed to be converted to free radicals by itself to form active oxygen in the plant body and shows rapid herbicidal efficacy.

(4) Those which are believed to exhibit herbicidal effects by inhibiting chlorophyll biosynthesis of plants and abnormally accumulating a photosensitizing peroxide substance in the plant body, such as a diphenylether type such as nitrofen, chlomethoxyfen, bifenox, acifluorfen, acifluorfen-sodium, fomesafen, fomesafen-sodium, oxyfluorfen, lactofen, aclonifen, ethoxyfen-ethyl, fluoroglycofen-ethyl or fluoroglycofen; a cyclic imide type such as chlorphthalim, flumioxazin, flumiclorac, flumiclorac-pentyl, cinidon-ethyl, fluthiacet or fluthiacet-methyl; and others such as oxadiargyl, oxadiazon, sulfentrazone, carfentrazone-ethyl, thidiazimin, pentoxazone, azafenidin, isopropazole, pyraflufen-ethyl, benzfendizone, butafenacil, saflufenacil, flupoxam, fluazolate, profluazol, pyraclonil, flufenpyr-ethyl, bencarbazone or ethyl [3-(2-chloro-4-fluoro-5-(3-methyl-2,6-dioxo-4-trifluoromethyl-3,6-dihydro-2H-pyrimidin-1-yl)phenoxy)pyridin-2-yloxy]acetate (SYN-523).

(5) Those which are believed to exhibit herbicidal effects characterized by bleaching activities by inhibiting chromogenesis of plants such as carotenoids, such as a pyridazinone type such as norflurazon, chloridazon or metflurazon; a pyrazole type such as pyrazolynate, pyrazoxyfen, benzofenap, topramezone or pyrasulfotole; and others such as amitrole, fluridone, flurtamone, diflufenican, methoxyphenone, clomazone, sulcotrione, mesotrione, tembotrione, tefuryltrione, bicyclopyrone, isoxaflutole, difenzoquat, difenzoquat-metilsulfate, isoxachlortole, benzobicyclon, picolinafen, beflubutamid, SW-065, KUH-110 or a compound disclosed in the claim of WO2005118530.

(6) Those which exhibit strong herbicidal effects specifically to gramineous plants, such as an aryloxyphenoxypropionic acid type such as diclofop-methyl, diclofop, pyriphenop-sodium, fluazifop-butyl, fluazifop, fluazifop-P, fluazifop-P-butyl, haloxyfop-methyl, haloxyfop, haloxyfop-etotyl, haloxyfop-P, haloxyfop-P-methyl, quizalofop-ethyl, quizalofop-P, quizalofop-P-ethyl, quizalofop-P-tefuryl, cyhalofop-butyl, fenoxaprop-ethyl, fenoxaprop-P, fenoxaprop-P-ethyl, metamifop-propyl, metamifop, clodinafop-propargyl, clodinafop or propaquizafop; a cyclohexanedione type such as alloxydim-sodium, alloxydim, clethodim, sethoxydim, tralkoxydim, butroxydim, tepraloxydim, profoxydim or cycloxydim; and others such as flamprop-M-methyl, flamprop-M or flamprop-M-isopropyl.

(7) Those which are believed to exhibit herbicidal effects by inhibiting an amino acid biosynthesis of plants, such as a sulfonylurea type such as chlorimuron-ethyl, chlorimuron, sulfometuron-methyl, sulfometuron, primisulfuron-methyl, primisulfuron, bensulfuron-methyl, bensulfuron, chlorsulfuron, metsulfuron-methyl, metsulfuron, cinosulfuron, pyrazosulfuron-ethyl, pyrazosulfuron, azimsulfuron, rimsulfuron, nicosulfuron, flazasulfuron, imazosulfuron, cyclosulfamuron, prosulfuron, flupyrsulfuron-methyl-sodium, flupyrsulfuron, triflusulfuron-methyl, triflusulfuron, halosulfuron-methyl, halosulfuron, thifensulfuron-methyl, thifensulfuron, ethoxysulfuron, oxasulfuron, ethametsulfuron, ethametsulfuron-methyl, iodosulfuron, iodosulfuron-methyl-sodium, sulfosulfuron, triasulfuron, tribenuron-methyl, tribenuron, tritosulfuron, foramsulfuron, trifloxysulfuron, trifloxysulfuron-sodium, mesosulfuron-methyl, mesosulfuron, orthosulfamuron, flucetosulfuron, amidosulfuron, propyrisulfuron, metazosulfuron, iofensulfuron or a compound disclosed in the claim of EP0645386; a triazolopyrimidinesulfonamide type such as flumetsulam, metosulam, diclosulam, cloransulam-methyl, florasulam, penoxsulam or pyroxsulam; an imidazolinone type such as imazapyr, imazapyr-isopropylammonium, imazethapyr, imazethapyr-ammonium, imazaquin, imazaquin-ammonium, imazamox, imazamox-ammonium, imazamethabenz, imazamethabenz-methyl or imazapic; a pyrimidinylsalicylic acid type such as pyrithiobac-sodium, bispyribac-sodium, pyriminobac-methyl, pyribenzoxim, pyriftalid or pyrimisulfan; a sulfonylaminocarbonyltriazolinone type such as flucarbazone, flucarbazone-sodium, propoxycarbazone-sodium, propoxycarbazone or thiencarbazone; and others such as glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, glufosinate-P, glufosinate-P-ammonium, glufosinate-P-sodium, bilanafos, bilanafos-sodium, cinmethylin or triafamone.

(8) Those which are believed to exhibit herbicidal effects by inhibiting cell mitoses of plants, such as a dinitroaniline type such as trifluralin, oryzalin, nitralin, pendimethalin, ethalfluralin, benfluralin, prodiamine, butralin or dinitramine; an amide type such as bensulide, napropamide, propyzamide or pronamide; an organic phosphorus type such as amiprofos-methyl, butamifos, anilofos or piperophos; a phenyl carbamate type such as propham, chlorpropham, barban or carbetamide; a cumylamine type such as daimuron, cumyluron, bromobutide or methyldymron; and others such as asulam, asulam-sodium, dithiopyr, thiazopyr, chlorthal-dimethyl, chlorthal or diphenamid.

(9) Those which are believed to exhibit herbicidal effects by inhibiting protein biosynthesis or lipid biosynthesis of plants, such as a chloroacetamide type such as alachlor, metazachlor, butachlor, pretilachlor, metolachlor, S-metolachlor, thenylchlor, pethoxamid, acetochlor, propachlor, dimethenamid, dimethenamid-P, propisochlor or dimethachlor; a thiocarbamate type such as molinate, dimepiperate, pyributicarb, EPTC, butylate, vernolate, pebulate, cycloate, prosulfocarb, esprocarb, thiobencarb, diallate, tri-allate or orbencarb; and others such as etobenzanid, mefenacet, flufenacet, tridiphane, cafenstrole, fentrazamide, oxaziclomefone, indanofan, benfuresate, pyroxasulfone, fenoxasulfone, dalapon, dalapon-sodium, TCA-sodium or trichloroacetic acid.

(10) MSMA, DSMA, CMA, endothall, endothall-dipotassium, endothall-sodium, endothall-mono(N,N-dimethylalkylammonium), ethofumesate, sodium chlorate, pelargonic acid, nonanoic acid, fosamine, fosamine-ammonium, pinoxaden, ipfencarbazone , aclolein, ammonium sulfamate, borax, chloroacetic acid, sodium chloroacete, cyanamide, methylarsonic acid, dimethylarsinic acid, sodium dimethylarsinate, dinoterb, dinoterb-ammonium, dinoterb-diolamine, dinoterb-acetate, DNOC, ferrous sulfate, flupropanate, flupropanate-sodium, isoxaben, mefluidide, mefluidide-diolamine, metam, metam-ammonium, metam-potassium, metam-sodium, methyl isothiocyanate, pentachlorophenol, sodium pentachlorophenoxide, pentachlorophenol laurate, quinoclamine, sulfuric acid, urea sulfate, methiozolin, etc.

(11) Those which are believed to exhibit herbicidal effects by being parasitic on plants, such as *Xanthomonas campestris, Epicoccosirus nematosorus, Epicoccosirus nematosperus, Exserohilum monoseras* or *Drechsrela monoceras*.

In the present invention, in a case where compound A or its salt is formulated with various additives, or in a case where compound A or its salt and compound B are formulated together with various additives, it may be formulated into various formulations such as wettable powders, water dispersible granules, water-based suspensions, oil-based suspensions, gel formulation, emulsifiable concentrates, soluble concentrates, liquid formulation, emulsions, microemulsions, suspoemulsions and composite emulsions. The additives which can be used may be any additives so long as they are used in this technical field, and they may, for example, be a surfactant, a carrier, a solvent, a vegetable oil, a mineral oil, an anti-settling agent, a thickener, an anti-foaming agent, an anti-freezing agent, an antioxidant agent, an oil absorb agent, a gelling agent, a filler, a dispersion stabilizer, an anti-mold agent, a binder, a stabilizer, a disintegrator, a preservative agent and an inorganic ammonium salt. Specific examples of the additives include the following compounds. The herbicidal composition can be formulated in accordance with a conventional method in this technical field.

The surfactant may, for example, be an anionic surfactant such as a salt of fatty acid, a benzoate, an alkylsulfosuccinate, a dialkylsulfosuccinate, a polycarboxylate, a salt of alkyl sulfuric acid ester, an alkyl sulfate, an alkyl aryl sulfate, an alkyl diglycol ether sulfate, a salt of alcohol sulfuric acid ester, an alkyl sulfonate, an alkyl aryl sulfonate, an aryl sulfonate, a lignin sulfonate, an alkyl diphenyl ether disulfonate, a polystyrene sulfonate, a salt of alkyl phosphoric acid ester, an alkyl aryl phosphate, a styryl aryl phosphate, a salt of polyoxyethylene (POE) alkyl ether sulfuric acid ester, a POE alkyl aryl ether sulfate, a POE styryl aryl ether sulfate, a POE styryl aryl ether sulfonate, an ammonium salt of POE styryl aryl ether sulfate, a salt of POE alkyl aryl ether sulfuric acid ester, a POE alkyl ether phosphate, a salt of POE alkyl aryl phosphoric acid ester, a POE styryl aryl ether phosphoric acid ester or its salt, a salt of naphthalene sulfonic acid condensed with formaldehyde, or a salt of alkylnaphthalene sulfonic acid condensed with formaldehyde; a nonionic surfactant such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a POE alkyl ether, a POE aryl ether, a POE alkyl aryl ether, a POE styryl aryl ether, a POE glycol alkyl ether, a POE alkyl ester, a POE sorbitan alkyl ester, a POE sorbitol alkyl ester, a POE fatty acid ester, a POE sorbitan fatty acid ester, a POE sorbitol fatty acid ester, a POE glycerin fatty acid ester, POE hydrogenated castor oil, POE castor oil or a polyoxypropylene fatty acid ester; or a cationic surfactant such as an alkoxylated fatty amine, and they may be used as a mixture of two or more if desired.

The carrier or the filler may, for example, be diatomaceous earth, slaked lime, calcium carbonate, talc, white carbon, kaolin, bentonite, a mixture of kaolinite and sericite, clay, sodium carbonate, sodium bicarbonate, mirabilite, zeolite, starch, sodium chloride, ammonium phosphate, ammonium sulfate, ammonium chloride, sugar, urea, lactose or glucose, and they may be used as a mixture of two or more if desired.

The solvent may, for example, be water, solvent naphtha, paraffin, dioxane, acetone, isophorone, methyl isobutyl ketone, cyclohexane, dimethyl sulfoxide, dimethyl formamide, N-methyl-2-pyrolidone, an alcohol, acetic acid, butyric acid, isopropyl acetate, butyl acetate, alkylbenzene, alkylnaphthalene or a glycol. They may be used as a mixture of two or more if desired.

The vegetable oil may, for example, be olive oil, kapok oil, castor oil, papaya oil, camelia oil, coconut oil, sesame oil, corn oil, rice bran oil, peanut oil, cottonseed oil, soybean oil, rapeseed oil, linseed oil, tung oil, sunflower oil, safflower oil, a fatty acid derived from the above-described respective oils, or an alkyl ester of the fatty acid, and the mineral oil may, for example, be an aliphatic hydrocarbon such as liquid paraffin or paraffin petroleum, or an aromatic hydrocarbon such as an alkylbenzene or an alkylnaphthalene, and they may be used as a mixture of two or more if desired. The above-described fatty acid may, for example, be a $C_{12-22}$ saturated or unsaturated fatty acid such as lauric acid, palmitic acid, stearic acid, oleic acid, linoleic acid, linolenic acid, erucic acid or brassidic acid, and the alkyl ester thereof may be a $C_{1-18}$ linear or branched alkyl ester such as a methyl ester, a butyl ester, an isobutyl ester or an oleyl ester.

The anti-settling agent may, for example, be silica, organic bentonite (bentonite-alkylamino complex), bentonite, white carbon or aluminum magnesium silicate, and they may be used as a mixture of two or more if desired.

The thickener may, for example, be a heteropolysaccharide such as xanthan gum or guar gum, a water-soluble polymer such as polyvinyl alcohol, carboxymethylcellulose sodium salt or sodium alginate, or bentonite or white carbon, and they may be used as a mixture of two or more if desired.

The anti-foaming agent may, for example, be polydimethylsiloxane or acetylene alcohol, and they may be used as a mixture of two or more if desired.

The anti-freezing agent may, for example, be ethylene glycol, propylene glycol, glycerin or urea, and they may be used as a mixture of two or more if desired.

The oil absorb agent may, for example, be silicon dioxide, starch hydrolysate, kaolin, clay, talc, diatomaceous earth, artificial diatomaceous earth/lime, asbestos, a mixture of kaolinite and sericite, calcium silicate, precipitated calcium carbonate light, silicificated precipitated calcium carbonate light, acid clay, carbon black, natural earthy graphite, pearlite product, ultrafine aluminum oxide anhydrous particles, ultrafine titanium oxide particles, basic magnesium carbonate, magnesium aluminosilicate, a silica/alumina synthetic filler or magnesium silicate hydrate, and they may be used as a mixture of two or more if desired.

The gelling agent may, for example, be silica, organic attapulgite, clay, hydrogenated castor oil, a higher fatty acid ester, a higher alcohol, a salt of dialkylsulfosuccinic acid ester, a salt of benzoic acid, an alkyl sulfate, a mixture of a polyacrylic polymer or a polyacrylic copolymer and water, or 12-hydroxystearic acid, and they may be used as a mixture of two or more if desired.

The binder may, for example, be lignin sulfonate, xanthan gum, carboxymethylcellulose or starch, and they may be used as a mixture of two or more if desired.

The disintegrator may, for example, be an inorganic salt such as carboxymethyl cellulose calcium salt, ammonium sulfate, potassium chloride or magnesium chloride, or one having disintegrating effect among the above-mentioned surfactants, such as sodium lauryl sulfate, sodium dodecylbenzene sulfonate or ammonium polyacrylate, and they may be used as a mixture of two or more if desired.

The preservative agent may, for example, be formaldehyde, parachlorometaxylenol or 1,2-benzoisothiazolin-3-one, and they may be used as a mixture of two or more if desired.

In the above various formulations, the blend ratio of the respective components cannot be generally be defined, as it varies depending upon various conditions such as the type of the components, the type of the formulation, and the application site. For example, compound A or its salt is blended in a ratio of preferably from 0.1 to 95 parts by weight, more preferably from 2 to 85 parts by weight, and as the rest, the additives are blended in a ratio of preferably from 5 to 99.9 parts by weight, more preferably from 15 to 98 parts by weight. Further, in a case where compound B is blended in a ratio of preferably from 0.1 to 94.9 parts by weight, more preferably from 5 to 60 parts by weight if desired, and another herbicidal compound is blended in a ratio of preferably from 0.1 to 94.9 parts by weight, more preferably from 0.5 to 75 parts by weight if desired, the additives are blended as the rest, so that the total amount is 100 parts by weight. The blend ratios of the respective components in several formulations are mentioned below, however, the present invention is not limited to such specific formulations.

In the case of a water-based suspension, compound A or its salt is blended in a ratio of preferably from 0.1 to 60 parts by weight, more preferably from 2 to 50 parts by weight, the surfactant is blended in a ratio of preferably from 0.5 to 20 parts by weight, more preferably from 1 to 15 parts by weight, and as the rest, water is blended in a ratio of preferably from 25 to 99.4 parts by weight, more preferably from 30 to 97 parts by weight to prepare a water-based suspension. Further, in a case where compound B is blended in a ratio of preferably from 0.1 to 60 parts by weight, more preferably from 5 to 40 parts by weight if desired, another herbicidal compound is blended in a ratio of preferably from 0.1 to 60 parts by weight, more preferably from 0.5 to 30 parts by weight if desired, an anti-foaming agent is blended in a ratio of preferably from 0.05 to 3 parts by weight, more preferably from 0.1 to 1 part by weight if desired, an anti-freezing agent is blended in a ratio of preferably from 0.5 to 10 parts by weight, more preferably from 2 to 10 parts by weight if desired, an anti-settling agent is blended in a ratio of preferably from 0.1 to 5 parts by weight, more preferably from 0.5 to 3 parts by weight if desired, a thickener is blended in a ratio of preferably from 0.1 to 5 parts by weight, more preferably from 0.1 to 2 parts by weight if desired, and a preservative agent is blended in a ratio of preferably from 0.01 to 1 part by weight, more preferably from 0.05 to 0.2 part by weight if desired, water is blended as the rest so that the total amount is 100 parts by weight to prepare a water-based suspension.

In the case of an oil-based suspension, compound A or its salt is blended in a ratio of preferably from 0.1 to 40 parts by weight, more preferably from 2 to 35 parts by weight, the surfactant is blended in a ratio of preferably from 1 to 30 parts by weight, more preferably from 1 to 25 parts by weight, and as the rest, a vegetable oil or a mineral oil is blended in a ratio of preferably from 10 to 98.9 parts by weight, more preferably from 20 to 97 parts by weight to prepare an oil-based suspension. Further, in a case where compound B is blended in a ratio of preferably from 0.1 to 80 parts by weight, more preferably from 5 to 60 parts by weight if desired, another herbicidal compound is blended in a ratio of preferably from 0.1 to 40 parts by weight, more preferably from 0.5 to 30 parts by weight if desired, and an anti-settling agent is blended in a ratio of preferably from 0.1 to 5 parts by weight, more preferably from 0.5 to 3 parts by weight if desired, a vegetable oil or a mineral oil is blended as the rest so that the total amount is 100 parts by weight to prepare an oil-based suspension.

In the case of a wettable powder, compound A or its salt is blended in a ratio of preferably from 0.1 to 95 parts by weight, more preferably from 5 to 85 parts by weight, the surfactant is blended in a ratio of preferably from 0.5 to 40 parts by weight, more preferably from 5 to 30 parts by weight, and as the rest, a carrier or a filler is blended in a ratio of preferably from 4.5 to 99.4 parts by weight, more preferably from 10 to 90 parts by weight to prepare a wettable powder. Further, in a case where compound B is blended in a ratio of preferably from 0.1 to 94.9 parts by weight, more preferably from 10 to 60 parts by weight if desired, another herbicidal compound is blended in a ratio of preferably from 0.1 to 94.9 parts by weight, more preferably from 0.5 to 75 parts by weight if desired, and an oil absorb agent is blended in a ratio of preferably from 1 to 90 parts by weight, more preferably from 1 to 50 parts by weight if desired, a carrier or a filler is blended as the rest so that the total amount is 100 parts by weight to prepare a wettable powder.

Preferred embodiments of the present invention will be described below, but the present invention is by no means restricted thereto.

1. A herbicidal composition comprising (1) compound A or its salt and (2) compound B.
2. A herbicidal composition for wheat, comprising (1) compound A or its salt and (2) compound B.
3. A herbicidal composition for corn, comprising (1) compound A or its salt and (2) compound B.
4. A herbicidal composition for at least one cool season turfgrass selected from the group consisting of kentucky bluegrass, perennial ryegrass and bentgrass, comprising (1) compound A or its salt and (2) compound B.
5. The herbicidal composition according to any one of the above 1 to 4, which further contains (3) another herbicidal compound.
6. The herbicidal composition according to the above 5, wherein (3) another herbicidal compound is pyridate.
7. The herbicidal composition according to the above 5, wherein (3) another herbicidal compound is bromoxynil, its alkyl ester or its salt.
8. A method for controlling undesired plants, which comprises applying a herbicidally effective amount of (1) compound A or its salt and an amount effective as a safener of (2) compound B, to the undesired plants or to a place where they grow.
9. A method for controlling undesired plants in wheat fields, which comprises applying a herbicidally effective amount of (1) compound A or its salt and an amount effective as a safener of (2) compound B, to the undesired plants or to a place where they grow.
10. A method for controlling undesired plants in corn fields, which comprises applying a herbicidally effective amount of (1) compound A or its salt and an amount effective as a safener of (2) compound B, to the undesired plants or to a place where they grow.
11. A method for controlling undesired plants in lawn fields where at least one cool season turfgrass selected from the group consisting of kentucky bluegrass, perennial ryegrass and bentgrass grows, which comprises applying a herbicidally effective amount of (1) compound A or its salt and an amount effective as a safener of (2) compound B, to the undesired plants or to a place where they grow.
12. The method according to any one of the above 8 to 11, wherein a herbicidally effective amount of (3) another herbicidal compound is further applied.
13. The method according to the above 12, wherein (3) another herbicidal compound is pyridate.
14. The method according to the above 12, wherein (3) another herbicidal compound is bromoxynil, its alkyl ester or its salt.
15. A method for improving the safety of (1) compound A or its salt for wheat by (2) compound B.
16. A method for improving the safety of (1) compound A or its salt for corn by (2) compound B.
17. The method for improving the safety of (1) compound A or its salt for at least one cool season turfgrass selected from the group consisting of kentucky bluegrass, perennial ryegrass and bentgrass by (2) compound B.
18. A method for reducing an undesired effect of (1) compound A or its salt against wheat by (2) compound B.

19. A method for reducing an undesired effect of (1) compound A or its salt against corn by (2) compound B.

20. A method for reducing an undesired effect of (1) compound A or its salt against at least one cool season turfgrass selected from the group consisting of kentucky bluegrass, perennial ryegrass and bentgrass, by (2) compound B.

21. A herbicidal composition for at least one cool season turfgrass selected from the group consisting of kentucky bluegrass, perennial ryegrass and bentgrass, for wheat, for corn or for timothy, which comprises (1) compound A or its salt and (2) compound B in a weight ratio of from 1:0.1 to 1:0.5.

22. A herbicidal composition for at least one cool season turfgrasses selected from the group consisting of kentucky bluegrass, perennial ryegrass and bentgrass, which comprises (1) compound A or its salt and (2) compound B in a weight ratio of from 1:0.1 to 1:0.5.

23. A herbicidal composition for wheat or for corn, which comprises (1) compound A or its salt and (2) compound B in a weight ratio of from 1:0.1 to 1:0.5.

24. A herbicidal composition for wheat, which comprises (1) compound A or its salt and (2) compound B in a weight ratio of from 1:0.1 to 1:0.5.

25. A herbicidal composition for timothy, which comprises (1) compound A or its salt and (2) compound B in a weight ratio of from 1:0.1 to 1:0.5.

26. A method for controlling undesired plants in cultivation or growth control of at least one cool season turfgrass selected from the group consisting of kentucky bluegrass, perennial ryegrass and bentgrass, of wheat, of corn or of timothy, which comprises applying (1) compound A or its salt in an amount of from 50 to 150 g/ha and (2) compound B in an amount of from 10 to 75 g/ha.

27. A method for controlling undesired plants in cultivation or growth control of at least one cool season turfgrass selected from the group consisting of kentucky bluegrass, perennial ryegrass and bentgrass, which comprises applying (1) compound A or its salt in an amount of from 50 to 150 g/ha and (2) compound B in an amount of from 10 to 75 g/ha.

28. A method for controlling undesired plants in cultivation or growth control of wheat or corn, which comprises applying (1) compound A or its salt in an amount of from 50 to 150 g/ha and (2) compound B in an amount of from 10 to 75 g/ha.

29. A method for controlling undesired plants in cultivation or growth control of wheat, which comprises applying (1) compound A or its salt in an amount of from 50 to 150 g/ha and (2) compound B in an amount of from 10 to 75 g/ha.

30. A method for controlling undesired plants in cultivation or growth control of timothy, which comprises applying (1) compound A or its salt in an amount of from 50 to 150 g/ha and (2) compound B in an amount of from 10 to 75 g/ha.

31. The herbicidal composition according to the above 5, wherein (3) another herbicidal compound is at least one compound selected from the group consisting of 2,4-D, 2,4-D-ethyl, dicamba, clopyralid, linuron, atrazine, terbuthylazine, bromoxynil-octanoate, pyridate, bentazone-sodium, carfentrazone-ethyl, sulcotrione, mesotrione, rimsulfuron, nicosulfuron, prosulfuron, halosulfuron-methyl, thifensulfuron-methyl, glyphosate-potassium, glyphosate-ammonium, glufosinate-ammonium, pendimethalin, alachlor, S-metolachlor, pethoxamid, acetochlor, flufenacet, pyroxasulfone and pinoxaden.

32. The herbicidal composition according to the above 5, wherein (3) another herbicidal compound is nicosulfuron.

33. The method according to the above 12, wherein (3) another herbicidal compound is at least one compound selected from the group consisting of 2,4-D, 2,4-D-ethyl, dicamba, clopyralid, linuron, atrazine, terbuthylazine, bromoxynil-octanoate, pyridate, bentazone-sodium, carfentrazone-ethyl, sulcotrione, mesotrione, rimsulfuron, nicosulfuron, prosulfuron, halosulfuron-methyl, thifensulfuron-methyl, glyphosate-potassium, glyphosate-ammonium, glufosinate-ammonium, pendimethalin, alachlor, S-metolachlor, pethoxamid, acetochlor, flufenacet, pyroxasulfone and pinoxaden.

34. The method according to the above 12, wherein (3) another herbicidal compound is nicosulfuron.

EXAMPLES

Now, the present invention will be described in further detail with reference to Examples. However, it should be understood that the present invention is by no means restricted to such specific Examples.

Example 1

(1) Compound A (purity 99.6%): 36.26 parts by weight
(2) Alkylnaphthalene sulfonate condensed with formaldehyde (tradename: Morwet D425 manufactured by AkzoNobel): 2.21 parts by weight
(3) POE styryl phenyl ether phosphate potassium salt (tradename: Soprophor FLK/70 manufactured by Rhodia): 2.21 parts by weight
(4) Aluminum magnesium silicate (tradename: Veegum R manufactured by Sanyo Chemical Industries, Ltd.): 0.88 part by weight
(5) Propylene glycol: 6.19 parts by weight
(6) Dimethylpolysiloxane (tradename: Silcolapse 432 manufactured by Bluestar Silicones): 0.35 part by weight
(7) Xanthan gum (tradename: Rhodopol 23 manufactured by Rhodia): 0.09 part by weight
(8) 1,2-Benzisothiazolin-3-one (tradename: Proxel GXL manufactured by Arch Chemicals, Inc.): 0.04 part by weight
(9) Water: 51.77 parts by weight
The above components are mixed and pulverized by a wet pulverizer for 5 minutes to prepare a water-based suspension. This is diluted with water together with compound B and applied.

Example 2

(1) Compound A (purity: 99.6%): 36.26 parts by weight
(2) Morwet D425 (tradename): 2.65 parts by weight
(3) Ammonium POE styryl phenyl ether sulfonate (tradename: Soprophor 4D384 manufactured by Rhodia): 2.21 parts by weight
(4) Veegum R (tradename): 0.88 part by weight
(5) Propylene glycol: 6.19 parts by weight
(6) Silcolapse 432 (tradename): 0.35 part by weight
(7) Rhodopol 23 (tradename): 0.09 part by weight
(8) Proxel GXL (tradename): 0.04 part by weight
(9) Water: 51.33 parts by weight
The above components are mixed and pulverized by a wet pulverizer for 5 minutes to prepare a water-based suspension. This is diluted with water together with compound B and applied.

Example 3

(1) Compound A (purity: 99.6%): 36.26 parts by weight
(2) Morwet D425 (tradename): 2.21 parts by weight (3) POE/polyoxypropylene block copolymer (tradename: Pluronic PE10300 manufactured by BASF): 2.21 parts by weight
(4) Veegum R (tradename): 0.88 part by weight
(5) Propylene glycol: 6.19 parts by weight
(6) Silcolapse 432 (tradename): 0.35 part by weight
(7) Rhodopol 23 (tradename): 0.09 part by weight
(8) Proxel GXL (tradename): 0.04 part by weight
(9) Water: 51.77 parts by weight The above components are mixed and pulverized by a wet pulverizer for 5 minutes to prepare a water-based suspension. This is diluted with water together with compound B and applied.

Now, Test Examples will be described. Compound A, Compound B and other herbicidal compounds used in Test Examples are as follows. They can be prepared by a conventional method in this technical field, by the above-described preparation method, or the like.

Compound A: water-based suspension containing compound A (the above Example 1)

Fenchlorazole-ethyl: wettable powder containing fenchlorazole-ethyl (manufactured by Sigma-Aldrich Japan)

Isoxadifen-ethyl: wettable powder containing isoxadifen-ethyl (manufactured by Santa Cruz Biotechnology, inc.)

Mefenpyr-diethyl: wettable powder containing mefenpyr-diethyl (manufactured by Santa Cruz Biotechnology, inc.)

Cloquintocet-mexyl: wettable powder containing cloquintocet-mexyl (manufactured by Wako Pure Chemical Industries, Ltd.)

Cyprosulfamide: wettable powder containing cyprosulfamide (manufactured by Sigma-Aldrich Japan)

Bromoxynil-octanoate: CERTROL B (manufactured by Bayer CropScience AG)

Pyridate: Pyridate 600EC (manufactured by Belchim Crop Protection)

Test Example 1

Upland field soil was put into a 1/1,000,000 ha pot, and seeds of wheat (*Triticum aestivum* L.) were sown. When the wheat reached 2.3 to 2.5-leaf stage, predetermined amounts of compound A and fenchlorazole-ethyl, isoxadifen-ethyl, mefenpyr-diethyl, cloquintocet-mexyl or cyprosulfamide were diluted with water (in an amount corresponding to 300 L/ha) containing 0.5 vol % of an agricultural adjuvant (tradename: Destiny HC, manufactured by Winfield Solutions, LLC.) and applied for foliar treatment by a small sprayer.

On the seventh day after treatment, the state of growth of the wheat was visually observed to determine the growth inhibition rate (%) in accordance with the following evaluation standards. The results are shown in Table 1.

Growth inhibition rate (%)=0 (equivalent to the non-treated area) to 100 (complete kill)

TABLE 1

| compound A | compound B | | Growth inhibition rate |
|---|---|---|---|
| Dose (g/ha) | Compound | Dose (g/ha) | (%) of wheat |
| 100 | Fenchlorazole-ethyl | 10 | 2 |
| 100 | | 50 | 0 |
| 150 | | 75 | 2 |
| 100 | Isoxadifen-ethyl | 10 | 5 |
| 100 | | 50 | 2 |
| 150 | | 75 | 4 |

TABLE 1-continued

| compound A | compound B | | Growth inhibition rate |
|---|---|---|---|
| Dose (g/ha) | Compound | Dose (g/ha) | (%) of wheat |
| 100 | Mefenpyr-diethyl | 10 | 2 |
| 100 | | 50 | 0 |
| 150 | | 75 | 0 |
| 100 | Cloquintocet-mexyl | 10 | 7 |
| 100 | | 50 | 3 |
| 150 | | 75 | 10 |
| 100 | Cyprosulfamide | 10 | 3 |
| 150 | | 75 | 8 |
| 100 | Not added | | 40 |
| 150 | Not added | | 40 |

As evident from Table 1, the growth inhibition of the wheat caused by compound A was remarkably reduced by addition of compound B.

Test Example 2

Upland field soil was put into a 1/1,000,000 ha pot, and seeds of wheat (*Triticum aestivum* L.) were sown. When the wheat reached 2.0 to 2.2-leaf stage, predetermined amounts of compound A, another herbicidal compound and mefenpyr-diethyl or cloquintocet-mexyl were diluted with water (in an amount corresponding to 300 L/ha) containing 0.25 vol % of an agricultural adjuvant (tradename: Activator 90, manufactured by Loveland Products, Inc.) and applied for foliar treatment by a small sprayer.

On the seventh day after treatment, chlorosis which developed in the wheat was visually observed, and the results are shown in Table 2.

Degree of chlorosis=0 (equal to the non-treated area) to 5.0 (complete chlorosis)

TABLE 2

| Compound A Dose (g/ha) | Another herbicidal compound | | Compound B | | Chlorosis in wheat |
|---|---|---|---|---|---|
| | Compound | Dose (g/ha) | Compound | Dose (g/ha) | |
| 60 | Bromoxynil-octanoate | 480 | Mefenpyr-diethyl | 30 | 0 |
| | | | Cloquintocet-mexyl | 30 | 0 |
| | | | Not added | | 1.8 |
| 40 | Pyridate | 600 | Mefenpyr-diethyl | 20 | 0.3 |
| | | | Cloquintocet-mexyl | 20 | 0.2 |
| | | | Not added | | 1.8 |

As evident from Table 2, even when compound A and another herbicidal compound were used in combination, the chlorosis which developed in the wheat was not confirmed at all or was significantly reduced by addition of compound B.

Test Example 3

Upland field soil was put into a 1/1,000,000 ha pot, and seeds of perennial ryegrass (*Lolium perenne* L.) were sown. When the perennial ryegrass reached 1.7 to 2.2-leaf stage, predetermined amounts of compound A and fenchlorazole-ethyl, isoxadifen-ethyl, mefenpyr-diethyl or cloquintocet-mexyl were diluted with water (in an amount corresponding to 300

L/ha) containing 0.5 vol % of an agricultural adjuvant (tradename: Destiny HC, manufactured by Winfield Solutions, LLC.) and applied for foliar treatment by a small sprayer.

On the sixth day after treatment, chlorosis which developed in the perennial ryegrass was evaluated in the same manner as in the above Test Example 2. The results are shown in Table 3.

TABLE 3

| compound A | Compound B | | Chlorosis in |
|---|---|---|---|
| Dose (g/ha) | Compound | Dose (g/ha) | perennial ryegrass |
| 100 | Fenchlorazole-ethyl | 50 | 0 |
| 100 | Isoxadifen-ethyl | 50 | 0 |
| 100 | Mefenpyr-diethyl | 50 | 0 |
| 100 | Cloquintocet-mexyl | 50 | 0 |
| 100 | Not added | | 0.4 |

As evident from Table 3, the chlorosis which developed in the perennial ryegrass caused by compound A was not confirmed at all by addition of compound B.

Test Example 4

Upland field soil was put into a 1/1,000,000 ha pot, and seeds of timothy (*Phleum pratense* L.) were sown. When the timothy reached 1.6 to 2.0-leaf stage, predetermined amounts of compound A and isoxadifen-ethyl, mefenpyr-diethyl or cloquintocet-mexyl were diluted with water (in an amount corresponding to 300 L/ha) containing 0.5 vol % of an agricultural adjuvant (tradename: Destiny HC, manufactured by Winfield Solutions, LLC) and applied for foliar treatment by a small sprayer.

On the sixth day after treatment, the state of growth of the timothy was visually observed to evaluate the growth inhibition rate (%) in the same manner as in the above Test Example 1. The results are shown in Table 4.

TABLE 4

| Compound A | Compound B | | Growth inhibition rate |
|---|---|---|---|
| Dose (g/ha) | Compound | Dose (g/ha) | (%) of timothy |
| 100 | Isoxadifen-ethyl | 50 | 4 |
| 100 | Mefenpyr-diethyl | 50 | 0 |
| 100 | Cloquintocet-mexyl | 50 | 0 |
| 100 | Not added | | 10 |

As evident from Table 4, the growth inhibition of the timothy caused by compound A was remarkably reduced by addition of compound B.

Test Example 5

Upland field soil was put into a 1/1,000,000 ha pot, and turf of bentgrass (*Agrostis stolonifera* L.) was put. When the bentgrass reached a height of 2 mm, predetermined amounts of compound A and mefenpyr-diethyl or cloquintocet-mexyl were diluted with water (in an amount corresponding to 300 L/ha) containing 0.5 vol % of an agricultural adjuvant (tradename: Destiny HC, manufactured by Winfield Solutions, LLC.) and applied for foliar treatment by a small sprayer.

On the 24th day after treatment, the state of growth of the bentgrass was visually observed to determine the growth inhibition rate (%) in the same manner as in the above Test Example 1. The results are as shown Table 5.

TABLE 5

| Compound A | Compound B | | Growth inhibition of |
|---|---|---|---|
| Dose (g/ha) | Compound | Dose (g/ha) | bentgrass (%) |
| 100 | Mefenpyr-diethyl | 20 | 33 |
| 100 | | 50 | 23 |
| 100 | Cloquintocet-mexyl | 20 | 23 |
| 100 | | 50 | 23 |
| 100 | Not added | | 50 |

As evident from Table 5, the growth inhibition of the bentgrass caused by compound A was remarkably reduced by addition of compound B.

Test Example 6

Upland field soil was put into a 1/1,000,000 ha pot, and seeds of kentucky bluegrass (*Poa pratensis* L.) were sown. When the kentucky bluegrass reached 2-leaf stage, predetermined amounts of compound A and isoxadifen-ethyl, mefenpyr-diethyl or cloquintocet-mexyl were diluted with water (in an amount corresponding to 300 L/ha) containing 0.5 vol % of an agricultural adjuvant (tradename: Destiny HC, manufactured by Winfield Solutions, LLC) and applied for foliar treatment by a small sprayer.

On the seventh day after treatment, chlorosis which developed in the kentucky bluegrass was evaluated in the same manner as in the above Test Example 2. The results are as shown Table 6.

TABLE 6

| Compound A | Compound B | | Chlorosis in kentucky |
|---|---|---|---|
| Dose (g/ha) | Compound | Dose (g/ha) | bluegrass |
| 100 | Isoxadifen-ethyl | 50 | 0.7 |
| 100 | Mefenpyr-diethyl | 50 | 0.4 |
| 100 | Cloquintocet-mexyl | 50 | 0.6 |
| 100 | Not added | | 1.7 |

As evident from Table 6, the chlorosis which developed in the kentucky bluegrass caused by compound A was significantly reduced by addition of compound B.

INDUSTRIAL APPLICABILITY

According to the present invention, a herbicidal composition having improved safety for useful plants can be provided.

The entire disclosure of Japanese Patent Application No. 2013-134466 filed on Jun. 27, 2013 including specification, claims, drawings and abstract is incorporated herein by reference in its entirety.

The invention claimed is:

1. A herbicidal composition comprising component (1) 1-(1-ethyl-4-(3-(2-methoxyethoxy)-2-methyl-4-(methylsulfonyl)benzoyl)-1H-pyrazol-5-yloxy)ethyl methyl carbonate or its salt and component (2) at least one compound selected from the group consisting of fenchlorazole-ethyl, isoxadifen-ethyl, mefenpyr-diethyl, cloquintocet-mexyl and cyprosulfamide, which contains the component (1) and the component (2) in a weight ratio of from 1:0.05 to 1:2.

2. The herbicidal composition according to claim 1, which further contains (3) another herbicidal compound.

3. The herbicidal composition according to claim 1, which contains the component (1) and the component (2) in a weight ratio of from 1:0.1 to 1:1 for at least one cool season turfgrass selected from the group consisting of kentucky bluegrass, perennial ryegrass and bentgrass, for wheat, for corn or for timothy.

4. The herbicidal composition according to claim 1, which contains the component (1) and the component (2) in a weight ratio of from 1:0.1 to 1:1 for at least one cool season turfgrass selected from the group consisting of kentucky bluegrass, perennial ryegrass and bentgrass.

5. The herbicidal composition according to claim 1, which contains the component (1) and the component (2) in a weight ratio of from 1:0.1 to 1:1 for wheat or for corn.

6. A method for controlling undesired plants, which comprises applying a herbicidally effective amount of component (1) 1-(1-ethyl-4-(3-(2-methoxyethoxy)-2-methyl-4-(methylsulfonyl)benzoyl)-1H-pyrazol-5-yloxy)ethyl methyl carbonate or its salt and an amount effective as a safener of component (2) at least one compound selected from the group consisting of fenchlorazole-ethyl, isoxadifen-ethyl, mefenpyr-diethyl, cloquintocet-mexyl and cyprosulfamide, to the undesired plants or to a place where they grow, wherein the component (1) is applied in an amount of from 5 to 150 g/ha and the component (2) is applied in an amount of from 0.25 to 300 g/ha to control the undesired plants.

7. The method according to claim 6, wherein a herbicidally effective amount of (3) another herbicidal compound is further applied.

8. The method according to claim 6, wherein the component (1) is applied in the amount of from 5 to 150 g/ha and the component (2) is applied in the amount of from 0.25 to 300 g/ha to control the undesired plants in cultivation or growth control of at least one cool season turfgrass selected from the group consisting of kentucky bluegrass, perennial ryegrass and bentgrass, of wheat, of corn or of timothy.

9. A method for improving the safety of component (1) 1-(1-ethyl-4-(3-(2-methoxyethoxy)-2-methyl-4-(methylsulfonyl)benzoyl)-1H-pyrazol-5-yloxy)ethyl methyl carbonate or its salt for useful plants by component (2) at least one compound selected from the group consisting of fenchlorazole-ethyl, isoxadifen-ethyl, mefenpyr-diethyl, cloquintocet-mexyl and cyprosulfamide, comprising applying, to the useful plants and/or undesired plants or to a place where they grow, component (1) in an amount of from 5 to 150 g/ha, and component (2) in an amount of from 0.25 to 300 g/ha.

10. The method according to claim 9, wherein the component (1) is applied in the amount of from 5 to 150 g/ha and the component (2) is applied in the amount of from 0.25 to 300 g/ha to improve the safety for cool season turfgrasses selected from kentucky bluegrass, perennial ryegrass and bentgrass, for wheat, for corn or for timothy.

11. A method for reducing an undesired effect of component (1) 1-(1-ethyl-4-(3-(2-methoxyethoxy)-2-methyl-4-(methylsulfonyl)benzoyl)-1H-pyrazol-5-yloxy)ethyl methyl carbonate or its salt against useful plants by component (2) at least one compound selected from the group consisting of fenchlorazole-ethyl, isoxadifen-ethyl, mefenpyr-diethyl, cloquintocet-mexyl and cyprosulfamide, comprising applying, to the useful plants and/or undesired plants or to a place where they grow, component (1) in an amount of from 5 to 150 g/ha, and component (2) in an amount of from 0.25 to 300 g/ha.

12. The method according to claim 11, wherein the component (1) is applied in the amount of from 5 to 150 g/ha and the component (2) is applied in the amount of from 0.25 to 300 g/ha to reduce an undesired effect against at least one cool season turfgrass selected from the group consisting of kentucky bluegrass, perennial ryegrass and bentgrass, against wheat, against corn or against timothy.

* * * * *